United States Patent [19]
Sangekar et al.

[11] Patent Number: 5,834,472
[45] Date of Patent: Nov. 10, 1998

[54] ANTIFUNGAL COMPOSITION WITH ENHANCED BIOAVAILABILITY

[75] Inventors: Surendra A. Sangekar, Union; Winston A. Vadino, Whitehouse Station, both of N.J.; Ping I. Lee, Radnor, Pa.

[73] Assignee: Schering Corporation, Kenilworth, N.J.

[21] Appl. No.: 861,250

[22] Filed: May 21, 1997

[51] Int. Cl.⁶ .......................... A61K 31/50; A61K 31/495
[52] U.S. Cl. ........................................ 514/252; 514/772.3
[58] Field of Search .............................................. 514/252

[56] References Cited

U.S. PATENT DOCUMENTS

| | | | |
|---|---|---|---|
| 4,791,111 | 12/1988 | Heeres et al. | 514/252 |
| 4,853,223 | 8/1989 | Graf et al. | 424/405 |
| 4,883,808 | 11/1989 | Fodor et al. | 514/468 |
| 4,906,478 | 3/1990 | Valentine et al. | 424/682 |
| 5,039,676 | 8/1991 | Saksena et al. | 514/254 |
| 5,272,137 | 12/1993 | Blase et al. | 514/54 |
| 5,411,745 | 5/1995 | Oshlack et al. | 424/456 |
| 5,506,248 | 4/1996 | Nikafar et al. | 514/374 |
| 5,580,578 | 12/1996 | Oshlacket | 424/468 |
| 5,661,151 | 8/1997 | Saksena et al. | 514/252 |

FOREIGN PATENT DOCUMENTS

| | | |
|---|---|---|
| 0539938A1 | 5/1993 | European Pat. Off. . |
| WO 89/04829 | 5/1989 | WIPO . |
| WO 95/17407 | 6/1995 | WIPO . |

OTHER PUBLICATIONS

Yamasaki et. al. Chemical Abstracts vol. 121: 117721u, 1994.

Jon E. Lutz et al., Activity of the Triazole 56592 against Disseminated Murine Coccidioidomycosis, Antimicrobial Agents and Chemotherapy, Jul. 1997, pp. 1558–1561.

Peter G. Welling, Pharmacokinetics, Processes and Mathematics, American Chemical Society, Washington, DC, ACS Monograph 185, (1986), p. 57.

J.G. nairn, Remington's Pharmaceutical Sciences, 18th edition, (1990), Mack Publishing Co., Chapter 83, p. 1519.

A.A. Nomeir et al., Bioavailability of SCH56592, a new broad spectrum triazole antifungl agent, from various formulations; Abstract of paper presented at 36th ICAAC, New Orleans, Louisiana, (Sep. 15–18, 1996); 1 page.

Pluronic® and Tetronic® Surfactants, publication of BASF Corporation, Mount Olive, New Jersey (1989), 29 pages.

Pluronic®Block Copolymer NF Grade (Poloxamer NF Grades); Technical Bulletin of BASF Corporation, (1995), 2 pages.

W. C. Gunsel and J. L. Kanig, Chapter 11, Tablets from The Theory and Practice of Industrial Pharmacy, 2nd Edition, Lea&Febiger, Philadelphia, (1976), pp. 321–344.

Van Hostetler and J.Q. Bellard, Chapter 13, Part I. Hard Tablets, from The Theory and Practice of Industrial Pharmacy, 2nd Edition, Lea&Febiger, Philadelphia, 1976, pp. 389–404.

A. K. Saksena et al., Concise Asymmetric Routes to 2,2, 4–Trisubstituted Tetrahydrofurans via Chiral Titanium Imide Enolates: Key Intermediates Towards Synthesis of Highly Active Azole Antifungals SCH51048 and SCH56592, Tetrahedron Letters, vol. 37, No. 32, (1996), pp. 5657–5660.

D. Loebenberg et al., #46, Formulation studies with SCH56592, a new broad spectrum antifungal triazole, abstract of paper submitted at "Focus on Fungal Infections 6" in New Orleans, Mar. 6–8, 1996, 4 pages.

*Primary Examiner*—Leonard Schenkman
*Attorney, Agent, or Firm*—Joseph T. Majka

[57] ABSTRACT

A pharmaceutical composition comprising:
 i) an antifungal agent which is (−)-(2R-cis)-4-[4-[4-[4-[[-5-(2,4-difluorophenyl)-tetrahydro-5-(1H-1,2,4-triazol-1-ylmethyl)furan-3-yl]methoxy]phenyl]-1-piperazinyl]phenyl]-2,4-dihydro-2-[(S)-1-ethyl-2(S)-hydroxypropyl]-3H-1,2,4-triazol-3-one;
 ii) at least one non-ionic surfactant; and
 iii) a diluent.

The composition enables the antifungal compound, which has very low water solubility, to have enhanced bioavailability in mammals, such as humans.

39 Claims, No Drawings

ANTIFUNGAL COMPOSITION WITH ENHANCED BIOAVAILABILITY

This application claims benefit of USC Provisional application Ser. No. 60/018,259, filed May 24, 1996.

BACKGROUND OF THE INVENTION

The present invention relates to compositions having enhanced or improved bioavailability for a novel triazole antifungal compound.

International Patent Publication Number Number WO 95/17407 published 29 Jun. 1995, teaches a novel class of tetrahydrofuran/triazole antifungal compounds. One particular compound, (2R-cis)-4-[4-[4-[4-[[-5-(2,4-difluorophenyl)-tetrahydro-5-(1H-1,2,4-triazol-1-ylmethyl)furan-3-yl]methoxy]phenyl]-1-piperazinyl]phenyl]2-4-dihydro-2-[(S)-1-ethyl-2(S)-hydroxypropyl]-3H-1,2,4-triazol-3-one, was found to have potent antifungal activity in aqueous suspensions against opportunistic fungi such as Aspergillis, Candida, Cryptococcus and other opportunistic fungi. However, non-aqueous compositions, such as powders or granules, were found to have reduced anti-fungal activity and/or bioavailability, presumably due to this compound's extremely low water solubility. It would be desirable to provide this antifungal compound in a pharmaceutical composition whose antifungal and/or bioavailabilty would be enhanced or improved.

SUMMARY OF THE INVENTION

The present invention is directed to a pharmaceutical composition comprising:
 i) an antifungal agent which is:

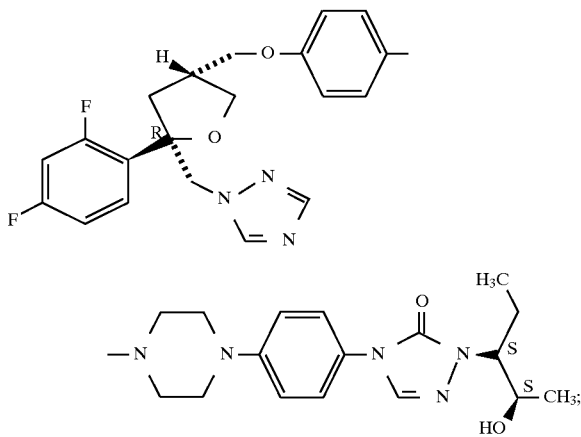

ii) at least one non-ionic surfactant; and
 iii) a diluent.

The pharmaceutical composition can also contain other optional excipients such as iv) disintegrants, v) binders, vi) lubricants, glidents and/or coloring agents known to those skilled in the art. The pharmaceutical composition can also be formulated into any other suitable dosage form, such as capsules (either solid-filled, semi-solid filled or liquid filled), tablets, powders for constitution or oral gels.

In another embodiment, the present invention is directed towards a pharmaceutical composition comprising:
 about 18–50% by weight of the antifungal agent;
 about 9–50% by weight of at least one non-ionic surfactant;
 about 12–60% by weight of a diluent which is microcrystalline cellulose;
 about 4–10% by weight of a disintegrant which is sodium croscarmellose;
 about 3–6% by weight of a binder which is polyvinylpyrrolidone; and
 about 0.3–1.5% by weight of a lubricant which is magnesium stearate; and
 optionally about 3–8% by weight of sodium lauryl sulfate.

It has been surprisingly and unexpectedly found that the inclusion of a non-ionic surfactant in a pharmaceutical composition comprising, inter alia, the antifungal compound, can enhance the bioavailability of the antifungal compound (otherwise having extremely low water solubility).

It has also been found that the inclusion of a non-ionic surfactant in a pharmaceutical composition comprising, inter alia, the antifungal compound, can enhance the bioavailability of the antifungal compound, compared to aqueous suspensions. These results are truly surprising and unexpected, since known references, such as Peter G. Welling, Pharmacokinetics, Processes and Mathematics, American Chemical Society, Washington D.C., ACS Monograph 185, 1986, page 57, teaches that solutions and suspensions generally give rise to more satisfactory bioavailability than capsules or tablets. J. G. Nairn, Remington's Pharmaceutical Sciences, 18th Edition, 1990, Mack Publishing Co., Chapter 83, page 1519 also teaches that since drugs are absorbed in their dissolved state, frequently it is found that the absorption rate of oral dosage forms decreases in the following order: aqueous solution>aqueous suspension>capsule or tablet.

The present invention has the advantage of being able to provide the antifungal compound in a pharmaceutical composition that can conveniently be formulated into non-aqueous or "dry" dosage forms such as capsules, tablets or powders having effective antifungal activity and/or bioavailabilty.

DETAILED DESCRIPTION OF THE EMBODIMENTS

WO 95/17407 published 29 Jun. 1995 discloses antifungal compounds of the formula:

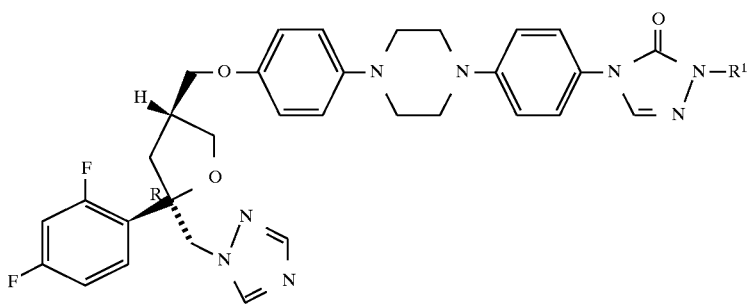

wherein $R^1$ is a straight or branch chain (C3 to C8) alkyl group substituted by one or two hydroxy moieties; esters and ethers thereof or a pharmaceutically acceptable salt thereof. An especially preferred compound of the above group taught in Examples 24 and 32 of WO 95/17407 is the antifungal compound, (−)-(2R-cis)-4-[4-[4-[4-[[-5-(2,4-difluorophenyl)-tetrahydro-5-(1H-1,2,4-triazol-1-ylmethyl)furan-3-yl]methoxy]phenyl]-1-piperazinyl]phenyl]2,-4-dihydro-2-[(S)-1-ethyl-2(S)-hydroxypropyl]-3H-1,2,4-triazol-3-one (hereinafter the antifungal compound); Formula: $C_{37}H_{42}F_2N_8O_4$; Molecular weight: 700.8; m.p. 164°–165° C., $[a]_D^{25}$ −29° C.±3° (c=1.0, $CHCl_3$), whose structure is depicted below:

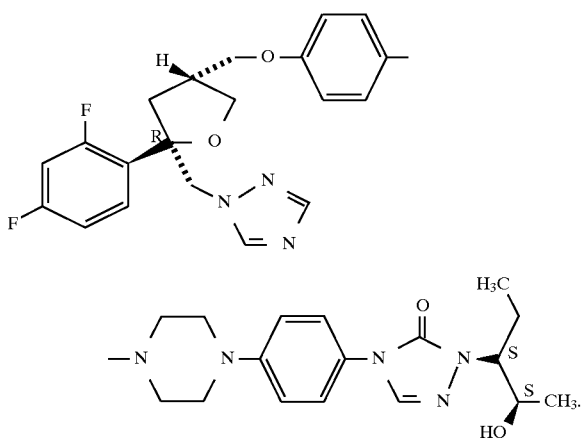

Micron-sized particles of the antifungal compound can be obtained either by the final step during the manufacture of the antifungal compound or by the use of conventional micronizing techniques after the conventional crystallization procedure(s).

Where micronizing techniques are employed, the antifungal compound may be micronized to the desired particle size range by conventional techniques, for example, using a ball mill, ultrasonic means, or preferably using fluid energy attrition mills such as the trost fluid energy mill from Plastomer Products, Newton, Pa. 18940. When using a fluid energy attrition mill, the desired particle size can be obtained by varying the feed rate of the antifungal into the mill.

About 99% of the of the micronized antifungal particle are less than or equal to 100 microns in length, of which 95% are less than or equal to 90 microns. Preferably, about 99% of the micronized particles are less than or equal to 50 microns, of which 95% are less than or equal to 40 microns. More preferably, 99% of the micronized particles are less than or equal to 20 microns, of which 95% are less than or equal to 10 microns.

The antifungal compound is employed in the composition in amounts effective to control the fungi of interest. Such amounts can range from about 2% to about 85% by weight of the composition, more preferably from 5% to about 80%, most preferably from about 18 to about 50% by weight. The amount of composition in the particular dosage form, e.g. capsule, tablet, etc., can range from about 10 to about 500 milligrams (mg) antifungal compound per dosage form, preferably from about 50 to about 200 mg. For example, the dosage form of a capsule can have about 50 or about 100 mg of the antifungal agent. Similarly, the dosage form of a tablet can have about 50 mg, about 100 mg or about 200 mg of the antifungal compound.

The pharmaceutical composition of the present invention can be formulated into any suitable dosage form, such as capsules (either solid-filled, semi-solid filled or liquid filled), tablets, powders for constitution or oral gels.

The following terms are used to describe the present pharmaceutical compositions, ingredients which can be employed in its formulation and methods for assessing its bioactivity or bioavailability.

Dosage form—composition containing the antifungal compound formulated into a delivery system, i.e., tablet, capsule, oral gel, powder for constitution or suspension in association with inactive ingredients.

Capsule—refers to a special container or enclosure made of methyl cellulose, polyvinyl alcohols, or denatured gelatins or starch for holding or containing compositions comprising the active antifungal compound. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredient (antifungal compound) with suitable diluents. The tablet can be prepared by compression of mixtures or granulations obtained by wet granulation, dry granulation or by compaction.

Oral gels—refers to the antifungal drug dispersed or solubilized in a hydrophillic semi-solid matrix.

Powders for constitution refers to powder blends containing the antifungal drug and suitable diluents which can be suspended in water or juices.

Surfactant—refers to a compound that can reduce the interfacial tension between two immiscible phases and this is due to the molecule containing two localized regions, one being hydrophilic in nature and the other hydrophobic.

Non-ionic surfactant—refers to a surfactant which lacks a net ionic charge and do not dissociate to an appreciable extent in aqueous media. The properties of non-ionic surfactants are largely dependent upon the proportions of the hydrophilic and hydrophobic groups in the molecule. Hydrophilic groups include the oxyethylene group (—OCH$_2$CH$_2$—) and the hydroxy group. By varying the number of these groups in a hydrophobic molecule, such as a fatty acid, substances are obtained which range from strongly hydrophobic and water insoluble compounds, such as glyceryl monostearate, to strongly hydrophilic and water-soluble compounds, such as the macrogols. Between these two extremes types include those in which the proportions of the hydrophilic and hydrophobic groups are more evenly balanced, such as the macrogol esters and ethers and sorbitan derivatives. Suitable non-ionic surfactants may be found in Martindale, The Extra Pharmacopoeia, 28th Edition, 1982, The Pharmaceutical Press, London, Great Britain, pp. 370 to 379. Such non-ionic surfactants include block copolymers of ethylene oxide and propylene oxide, glycol and glyceryl esters of fatty acids and their derivatives, polyoxyethylene esters of fatty acids (macrogol esters), polyoxyethylene ethers of fatty acids and their derivatives (macrogol ethers), polyvinyl alcohols, and sorbitan esters. Preferably, the non-ionic surfactant is a block copolymer of ethylene oxide and propylene oxide.

Suitable block copolymers of ethylene oxide and propylene oxide generically called "Poloxamers" and include those represented by the following chemical structure:

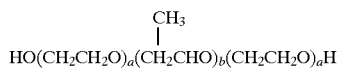

wherein a is an integer ranging from about 10 to about 110, preferably from about 12 to 101; more preferably from about 12 to 80; and b is an integer ranging from about 20 to about 60, more preferably from about 20 to about 56; also from about 20 to 27. Most preferably, a is 80 and b is 27, otherwise known as Pluronic®F68 surfactant, trademark of the BASF Corporation, Mount Olive, N.J., USA. Pluronic®F68 surfactant is also known as Poloxamer 188. This surfactant has an average molecular weight of 8400, is a solid at 20° C., has a viscosity (Brookfield) of 1000 cps at 77° C. Other suitable block copolymers of ethylene oxide and propylene oxide include Pluronic F87, also known as Poloxamer 237 wherein a is 64 and b is 37; and Pluronic F127, also known as Poloxamer 407 wherein a is 101 and b is 56.

Suitable glycol and glyceryl esters of fatty acids and their derivatives include glyceryl monooleate and similar water soluble derivatives;

Suitable polyoxyethylene esters of fatty acids (macrogol esters) include polyoxyethylene castor oil and hydrogenated castor oil derivatives;

Suitable polyoxyethylene ethers of fatty acids and their derivatives (macrogol ethers) include Cetomacrogel 1000, Lauromacrogols (a series of lauryl ethers of macrogols of differing chain lengths) e.g. Laureth 4, Laureth 9 and Lauromacrogol 400.

Suitable Sorbitan esters (esters of one or more of the hydroxyl groups in the sorbitans, with a fatty acid, such as stearic, palmitic, oleic or lauric acid) include, e.g. Polysorbate 20, Polysorbate 40, Polysorbate 60, Polysorbate 65, Polysorbate 80, Polysorbate 85, Sorbitan Monolaurate, Sorbitan Mono-oleate, Sorbitan Monopalmitate, Sorbitan Monostearate, Sorbitan Sesquioleate, Sorbitan Trioleate and Sorbitan Tristearate.

The amount of non-ionic surfactant in the composition can range from about 5 to about 50% by weight of the total composition, more preferably from about 5 to about 25% by weight.

Optionally, the present composition may also contain an anionic surfactant, e.g. sodium lauryl sulfate, the amount of which can range from about 1 to about 10% by weight of the total composition, more preferably from about 3 to about 8% by weight.

Diluent—refers to to substances that usually make up the major portion of the composition or dosage form. Suitable diluents include sugars such as lactose, sucrose, mannitol and sorbitol; starches derived from wheat, corn rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or theraputic moiety is absorbed into the systemic circulation from an administered dosage form as compared to a standard or control.

$C_{max}$ values refers to the maximum concentration of the antifungal compound measured (i.e. "peak") in the plasma serum.

AUC (0–72 hr) values refer to the area under the plasma/serum concentration-time curve for the antifungal over a designated time.

Conventional methods for preparing tablets are known. Such methods include dry methods such as direct compression and compression of granulation produced by compaction, or wet methods or other special procedures.

Compositions of the present invention can be prepared by mixing or granulating the antifungal compound with a non-ionic, polyethylene oxide and polypropylene oxide containing surfactant, together with the requisite amounts of a diluent, optionally with a disintegrant, lubricant, binder, glider and/or coloring agent. The above composition can then be used to fill capsules. Alternatively, the composition can be compressed into a tablet.

The following examples describe compositions of the present invention containing the antifungal compound, but they are not to be interpreted as limiting the scope of the claims.

EXAMPLE 1

Composition in Capsules

| Ingredient | mg/capsule | % wt basis |
|---|---|---|
| Antifungal compound | 100 | 19 |
| Pluronic F68 surfactant | 50 | 9.5 |
| microcrystalline cellulose | 300 | 56.9 |
| (a) sodium croscarmellose | 25 | 4.7 |
| polyvinylpyrollidone | 25 | 4.7 |
| (b) sodium croscarmellose | 25 | 4.7 |
| magnesium stearate | 2.5 | 0.5 |
|  | 527.5 | 100 |

EXAMPLE 2

Composition in Capsules

| Ingredient | mg/capsule | % wt basis |
|---|---|---|
| Antifungal compound | 100 | 25 |
| Pluronic F68 surfactant | 100 | 25 |
| microcrystalline cellulose | 136 | 34 |
| (a) sodium croscarmellose | 20 | 5 |
| polyvinylpyrollidone | 20 | 5 |
| (b) sodium croscarmellose | 20 | 5 |
| magnesium stearate | 4 | 1 |
|  | 400 | 100 |

Preparation of Capsules in Examples 1–2, 4–5, 10–12 and 15

Blend the antifungal compound, the Pluronic F68, the microcrystalline cellulose diluent, the (a) sodium croscarmellose disintegrant, and optionally, sodium lauryl sulfate as in Examples 10–12, in a suitable mixer for five to 10 minutes. Dissolve the polyvinylpyrollidone binder in water and granulate the above blend with the solution of polyvinylpyrollidone. Dry the granulated blend in a tray oven at a temperature of 45° to 50° C. overnight or fluid bed dry until the moisture content is less than 2%. Pass the granules through a 20 mesh screen and mix the milled granules for 5 minutes. Take a portion of the milled granules, mix with the magnesium stearate lubricant, screen, and then mix the screened granules with the remainder of the milled granules. Add (b) sodium croscarmellose and mix for 5 to 10 minutes. Fill the granules into suitable size capsules to the requisite fill weight.

EXAMPLE 3

Composition in Aqueous Suspension

Prepare a suspension containing 59.8 mg Pluronic F68 in four mL of distilled water. Add 200 mg of antifungal compound to the above solution and mix to give a homogeneous suspension.

Comparative Example. Capsules

| Ingredient | mg/capsule | % wt basis |
|---|---|---|
| Antifungal compound | 100.0 | 28.6 |
| Sodium lauryl sulfate surfactant | 22.5 | 6.4 |
| Microcrystalline cellulose | 178.0 | 50.9 |
| Sodium starch glycolate | 45.0 | 12.8 |
| Magnesium stearate | 4.5 | 1.3 |
|  | 350 | 100 |

Preparation of Capsules in Comparative Example.

Mix the antifungal compound, sodium lauryl sulfate (a surfactant), microcrystalline cellulose, and sodium starch glycolate in a blender for 10 minutes. Add magnesium stearate and mix for 5 minutes. Fill the granules into suitable size capsules to the requisite fill weight.

Testing for Bioavailability

Dogs are administered a 200 mg dose of the antifungal compound in two capsules or in suspension. Samples of serum are collected at selected times and analyzed by an HPLC/UV detection procedure using a high pressure liquid chromatograph equipped with an ultra-violet detector. In the table below, the $C_{max}$ and AUC (0–72 hr) values are indicators of the antifungal compound's bioavailability. The larger the AUC value, the greater the total amount of antifungal compound that accumulated in the plasma serum over the 72 hour period.

| Indicator of Bioavailability | Capsules Example 1 | Capsules Example 2 | Suspension Example 3 | Capsules Comparative Example |
|---|---|---|---|---|
| $C_{max}$ | 2.3 | 1.8 | 1.5 | 0.95 |
| $AUC_{(0-72\ hr)}$ ug/hr/ml | 92.5 | 69.4 | 59.3 | 29.72 |

The results above show that capsules of Examples 1 and 2 exhibit enhanced bioavailability over that of the aqueous suspension of Example 3 and especially over the capsules of the Comparative Example.

EXAMPLE 4

Composition in Capsules

| Ingredient | mg/capsule | % wt basis |
| --- | --- | --- |
| Antifungal compound | 50.00 | 19 |
| Pluronic F68 surfactant | 25.00 | 9.5 |
| microcrystalline cellulose | 150.00 | 56.9 |
| (a) sodium croscarmellose | 12.50 | 4.7 |
| polyvinylpyrollidone | 12.50 | 4.7 |
| (b) sodium croscarmellose | 12.50 | 4.7 |
| magnesium stearate | 1.25 | 0.5 |
| | 263.75 | 100 |

EXAMPLE 5

Composition in Capsules

| Ingredient | mg/capsule | % wt basis |
| --- | --- | --- |
| Antifungal compound | 100.00 | 22.2 |
| Pluronic F68 surfactant | 50.00 | 11.1 |
| microcrystalline cellulose | 245.25 | 54.5 |
| (a) sodium croscarmellose | 15.00 | 3.3 |
| polyvinylpyrollidone | 22.50 | 5.0 |
| (b) sodium croscarmellose | 15.00 | 3.3 |
| magnesium stearate | 2.25 | 0.5 |
| | 450.00 | 100 |

EXAMPLE 6

Composition in Tablets

| Ingredient | mg/tablet | % wt basis |
| --- | --- | --- |
| Antifungal compound | 100.00 | 22.2 |
| Pluronic F68 surfactant | 50.00 | 11.1 |
| microcrystalline cellulose | 245.25 | 54.5 |
| (a) sodium croscarmellose | 15.00 | 3.3 |
| polyvinylpyrollidone | 22.50 | 5.0 |
| (b) sodium croscarmellose | 15.00 | 3.3 |
| magnesium stearate | 2.25 | 0.5 |
| | 450.00 | 100 |

EXAMPLE 7

Composition in Tablets

| Ingredient | mg/tablet | % wt basis |
| --- | --- | --- |
| Antifungal compound | 100.0 | 19 |
| Pluronic F68 surfactant | 50.0 | 9.5 |
| microcrystalline cellulose | 300.0 | 56.9 |
| (a) sodium croscarmellose | 25.0 | 4.7 |
| polyvinylpyrollidone | 25.0 | 4.7 |
| (b) sodium croscarmellose | 25.0 | 4.7 |
| magnesium stearate | 2.5 | 0.5 |
| | 527.5 | 100 |

EXAMPLE 8

Composition in Tablets

| Ingredient | mg/tablet | % wt basis |
| --- | --- | --- |
| Antifungal compound | 200.0 | 19 |
| Pluronic F68 surfactant | 100.0 | 9.5 |
| microcrystalline cellulose | 600.0 | 56.9 |
| (a) sodium croscarmellose | 50.0 | 4.7 |
| polyvinylpyrollidone | 50.0 | 4.7 |
| (b) sodium croscarmellose | 50.0 | 4.7 |
| magnesium stearate | 5.0 | 0.5 |
| | 1025.0 | 100 |

EXAMPLE 9

Composition in Tablets

| Ingredient | mg/tablet | % wt basis |
| --- | --- | --- |
| Antifungal compound | 200.0 | 22.2 |
| Pluronic F68 surfactant | 100.0 | 11.1 |
| microcrystalline cellulose | 490.5 | 54.5 |
| (a) sodium croscarmellose | 30.0 | 3.3 |
| polyvinylpyrollidone | 45.0 | 5.0 |
| (b) sodium croscarmellose | 30.0 | 3.3 |
| magnesium stearate | 4.5 | 0.5 |
| | 900.0 | 100 |

Preparation of Tablets in Examples 6–9 and 13–14

Blend the antifungal compound, the Pluronic F68, the microcrystalline cellulose diluent, the (a) sodium croscarmellose disintegrant, and optionally, sodium lauryl sulfate as in Examples 13 and 14, in a suitable mixer for five to 10 minutes. Dissolve the polyvinylpyrollidone binder in water and granulate the above blend with the solution of polyvinylpyrollidone. Dry the granulated blend in a tray oven at a temperature of 45° to 50° C. overnight or fluid bed dry until the moisture content is less than 2%. Pass the granules through a 20 mesh screen and mix the milled granules for 5 minutes. Take a portion of the milled granules, mix with the magnesium stearate lubricant, screen, and then mix the screened granules with the remainder of the milled granules. Add (b) sodium croscarmellose and mix for 5 to 10 minutes. Compress the granules into a tablet of the requisite weight.

EXAMPLE 10

Composition in Capsules

| Ingredient | mg/capsule | % wt basis |
| --- | --- | --- |
| Antifungal compound | 200.00 | 44.44 |
| Pluronic F68 surfactant | 100.00 | 22.23 |
| Sodium lauryl sulfate | 30.00 | 6.67 |
| microcrystalline cellulose | 65.26 | 14.50 |
| (a) sodium croscarmellose | 15.00 | 3.33 |
| polyvinylpyrollidone | 22.50 | 5.00 |
| (b) sodium croscarmellose | 15.00 | 3.33 |
| magnesium stearate | 2.24 | 0.50 |
| | 450.00 | 100 |

EXAMPLE 11

Composition in Capsules

| Ingredient | mg/capsule | % wt basis |
|---|---|---|
| Antifungal compound | 100.00 | 44.44 |
| Pluronic F68 surfactant | 50.00 | 22.23 |
| Sodium lauryl sulfate | 15.00 | 6.67 |
| microcrystalline cellulose | 32.63 | 14.50 |
| (a) sodium croscarmellose | 7.50 | 3.33 |
| polyvinylpyrollidone | 11.25 | 5.00 |
| (b) sodium croscarmellose | 7.50 | 3.33 |
| magnesium stearate | 1.12 | 0.50 |
| | 225.00 | 100 |

EXAMPLE 12

Composition in Capsules

| Ingredient | mg/capsule | % wt basis |
|---|---|---|
| Antifungal compound | 100.00 | 26.67 |
| Pluronic F68 surfactant | 50.00 | 13.33 |
| Sodium lauryl sulfate | 15.00 | 4.00 |
| microcrystalline cellulose | 164.38 | 43.84 |
| (a) sodium croscarmellose | 12.50 | 3.33 |
| polyvinylpyrollidone | 18.75 | 5.00 |
| (b) sodium croscarmellose | 12.50 | 3.33 |
| magnesium stearate | 1.87 | 0.50 |
| | 375.00 | 100 |

EXAMPLE 13

Composition in Tablets

| Ingredient | mg/tablet | % wt basis |
|---|---|---|
| Antifungal compound | 100.00 | 22.22 |
| Pluronic F68 surfactant | 50.00 | 11.11 |
| Sodium lauryl sulfate | 30.00 | 6.67 |
| microcrystalline cellulose | 215.25 | 47.84 |
| (a) sodium croscarmellose | 15.00 | 3.33 |
| polyvinylpyrollidone | 22.50 | 5.00 |
| (b) sodium croscarmellose | 15.00 | 3.33 |
| magnesium stearate | 2.25 | 0.50 |
| | 450.00 | 100 |

EXAMPLE 14

Composition in Tablets

| Ingredient | mg/tablet | % wt basis |
|---|---|---|
| Antifungal compound | 200.00 | 22.22 |
| Pluronic F68 surfactant | 100.00 | 11.11 |
| Sodium lauryl sulfate | 30.00 | 6.67 |
| microcrystalline cellulose | 430.50 | 47.84 |
| (a) sodium croscarmellose | 30.00 | 3.33 |
| polyvinylpyrollidone | 45.00 | 5.00 |
| (b) sodium croscarmellose | 30.00 | 3.33 |
| magnesium stearate | 4.50 | 0.50 |
| | 450.00 | 100 |

EXAMPLE 15

Composition in Capsules

| Ingredient | mg/capsule | % wt basis |
|---|---|---|
| Antifungal compound | 100.00 | 26.67 |
| Pluronic F68 surfactant | 50.00 | 13.33 |
| microcrystalline cellulose | 179.38 | 47.84 |
| (a) sodium croscarmellose | 12.50 | 3.33 |
| polyvinylpyrollidone | 18.75 | 5.00 |
| (b) sodium croscarmellose | 12.50 | 3.33 |
| magnesium stearate | 1.87 | 0.50 |
| | 375.00 | 100 |

Examples 16 to 23. Composition in Capsules. Essentially the same procedure is employed as in Examples 1–2, 4–5, and 10–12 except that Pluronic F87 is substituted for Pluronic F68.

Examples 24 to 29. Composition in Tablets. Essentially the same procedure is employed as in Examples 6–9 and 13–14 except that Pluronic F127 is substituted for Pluronic F68.

What is claimed is:

1. A pharmaceutical composition comprising:

i) from about 2 to about 85% by weight of an antifungal agent which is:

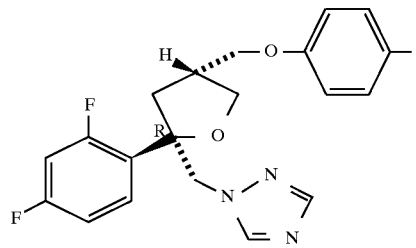

ii) from about 5 to about 50% by weight of at least one non-ionic surfactant that is a block copolymer of ethylene oxide and propylene oxide; and iii) from about 10 to about 90% by weight of a diluent.

2. The pharmaceutical composition of claim 1 wherein the non-ionic surfactant is a block copolymer of ethylene oxide and propylene oxide represented by the following chemical structure:

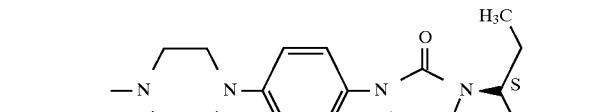

wherein a is an integer ranging from about 10 to about 110 and b is an integer ranging from about 20 to about 60.

3. The pharmaceutical composition of claim 2 wherein for the non-ionic surfactant, a is an integer ranging from about 12 to 80 and b is an integer ranging from about 20 to about 56.

4. The pharmaceutical composition of claim 3 wherein the amount of non-ionic surfactant in the composition ranges from about 5 to about 25% by weight.

5. The pharmaceutical composition of claim 2 wherein for the non-ionic surfactant, a is 80 and b is 27.

6. The pharmaceutical composition of claim 5 wherein the amount of the antifungal compound in the composition ranges about 5 to about 80% by weight.

7. The pharmaceutical composition of claim 6 wherein the antifungal compound is micronized.

8. The pharmaceutical composition of claim 5 wherein the amount of the antifungal compound in the composition ranges about 18 to about 50% by weight.

9. The pharmaceutical composition of claim 8 wherein the antifungal compound is micronized.

10. The pharmaceutical composition of claim 8 wherein the amount of non-ionic surfactant in the composition ranges from about 5 to about 25% by weight.

11. The pharmaceutical composition of claim 5 wherein the amount of non-ionic surfactant in the composition ranges from about 5 to about 25% by weight.

12. The pharmaceutical composition of claim 2 wherein the amount of non-ionic surfactant in the composition ranges from about 5 to about 25% by weight.

13. The pharmaceutical composition of claim 1 wherein the amount of non-ionic surfactant in the composition ranges from about 5 to about 25% by weight.

14. The pharmaceutical composition of claim 1 wherein the diluent is microcrystalline cellulose.

15. The pharmaceutical composition of claim 1 further comprising (iv) a disintegrant.

16. The pharmaceutical composition of claim 11 wherein the disintegrant is sodium croscarmellose.

17. The pharmaceutical composition of claim 15 further comprising (v) a binder.

18. The pharmaceutical composition of claim 17 wherein the binder is polyvinylpyrollidone.

19. The pharmaceutical composition of claim 17 further comprising (vi) a lubricant.

20. The pharmaceutical composition of claim 19 wherein the lubricant is magnesium stearate.

21. The pharmaceutical composition of claim 1 in the dosage form of a capsule, a tablet or a powder for constitution.

22. The pharmaceutical composition of claim 21 in the dosage form of a capsule having from about 10 to about 500 mg of the antifungal agent.

23. The pharmaceutical composition of claim 22 wherein the antifungal compound is micronized.

24. The pharmaceutical composition of claim 23 wherein the amount of non-ionic surfactant in the composition ranges from about 5 to about 25% by weight.

25. The pharmaceutical composition of claim 21 in the dosage form of a capsule having about 50 mg or about 100 mg of the antifungal agent.

26. The pharmaceutical composition of claim 25 wherein the antifungal compound is micronized.

27. The pharmaceutical composition of claim 24 wherein the amount of non-ionic surfactant in the composition ranges from about 5 to about 25% by weight.

28. The pharmaceutical composition of claim 21 in the dosage form of a tablet having from about 10 to about 500 mg of the antifungal agent.

29. The pharmaceutical composition of claim 28 wherein the antifungal compound is micronized.

30. The pharmaceutical composition of claim 29 wherein the amount of non-ionic surfactant in the composition ranges from about 5 to about 25% by weight.

31. The pharmaceutical composition of claim 21 wherein the antifungal compound is micronized.

32. The pharmaceutical composition of claim 31 wherein the amount of non-ionic surfactant in the composition ranges from about 5 to about 25% by weight.

33. The pharmaceutical composition of claim 21 in the dosage form of a tablet having about 50 mg, about 100 mg or about 200 mg of the antifungal agent.

34. The pharmaceutical composition of claim 33 wherein the antifungal compound is micronized.

35. The pharmaceutical composition of claim 34 wherein the amount of non-ionic surfactant in the composition ranges from about 5 to about 25% by weight.

36. The pharmaceutical composition of claim 1 wherein the antifungal compound is micronized.

37. The pharmaceutical composition of claim 36 wherein the amount of non-ionic surfactant in the composition ranges from about 5 to about 25% by weight.

38. A pharmaceutical composition comprising:

about 18–50% by weight of an antifungal agent of the formula

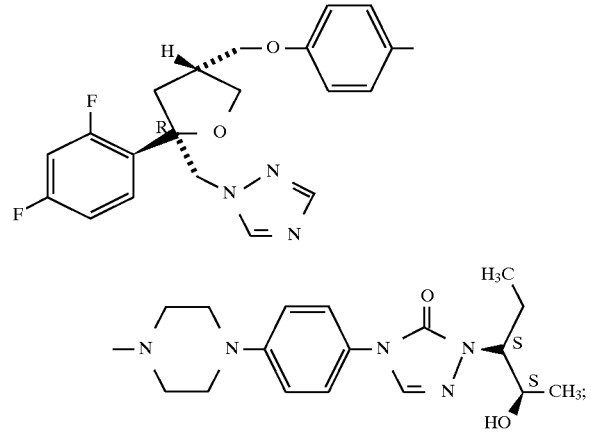

about 9–50% by weight of at least one non-ionic surfactant that is a block copolymer of ethylene oxide and propylene oxide;

about 12–60% by weight of a diluent which is microcrystalline cellulose;

about 4–10% by weight of a disintegrant which is sodium croscarmellose;

about 3–6% by weight of a binder which is polyvinylpyrrolidone;

about 0.3–1.5% by weight of a lubricant which is magnesium stearate; and optionally, about 3–8% by weight of sodium lauryl sulfate.

39. The pharmaceutical composition of claim 38 wherein the antifungal compound is micronized.

* * * * *